United States Patent [19]

Esteve-Subirana

[11] 4,005,220
[45] Jan. 25, 1977

[54] HEMOSTATIC COMPOSITIONS COMPRISING SALTS OF SUBSTITUTED HYDROQUINONE SULFONIC ACID

[75] Inventor: Antonio Esteve-Subirana, Barcelona, Spain

[73] Assignee: Laboratorios del Dr. Esteve, S.A., Barcelona, Spain

[22] Filed: Apr. 3, 1975

[21] Appl. No.: 564,735

Related U.S. Application Data

[62] Division of Ser. No. 441,415, Feb. 11, 1974.

[30] Foreign Application Priority Data

Feb. 20, 1973  Switzerland ............... 2395/73

[52] U.S. Cl. .................. 424/315; 424/316
[51] Int. Cl.² ............. A61K 31/185; A61K 31/205
[58] Field of Search ............... 424/315, 316
[56] References Cited

UNITED STATES PATENTS

| | | | |
|---|---|---|---|
| 3,436,462 | 4/1969 | Esteve-Subirana | 424/316 |
| 3,764,700 | 10/1973 | Esteve-Subirana | 424/315 |
| 3,873,606 | 3/1975 | Esteve-Subirana | 424/316 |

OTHER PUBLICATIONS

Burger, "Medicinal Chemistry" Second Edition, (1960) published by Interscience Publishers, Inc. N.Y. pp. 36, 42, & 43.

Chemical Abstracts vol. 64: 1996b; vol. 65: 1658n; vol. 69: 76933b and vol. 70: P77586y.

Primary Examiner—Donald B. Moyer
Attorney, Agent, or Firm—Henry L. Brinks

[57] ABSTRACT

Novel salts of substituted hydroquinone sulfonic acid having the general formula:

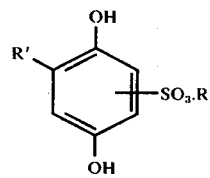

in which R denotes ammonium or a cation of an organic base such as alkylamines, alkanolamines, arylamines, alkylarylamines, aralkylamines and cyclamines, or a cation of an alkali or alkaline earth metal such as lithium, sodium, potassium, magnesium or calcium. The structure of course depends on the valency of R. In every case, R' denotes a linear or branched alkyl group with 1 to 6 carbon atoms. These salts are used as haemostatic agents and protective agents against capillary fragility.

14 Claims, No Drawings

HEMOSTATIC COMPOSITIONS COMPRISING SALTS OF SUBSTITUTED HYDROQUINONE SULFONIC ACID

This is a division of co-pending application Ser. No. 441,415 filed on Feb. 11, 1974 by the same inventors as herein.

The present invention relates to new salts of alkyl-p-dihydroxybenzenesulphonic acids, which possess noteworthy therapeutic properties.

The compounds of the invention corresponds to the general formula:

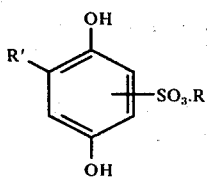

in which R denotes ammonium or a cation of an organic base such as alkylamines, alkanolamines, arylamines, alkylarylamines, aralkylamines and cyclamines, or a cation of an alkali or alkaline earth metal such as lithium, sodium, potassium, magnesium or calcium. The structure of course depends on the valency of R. In every case, R' denotes a linear or branched alkyl group with 1 to 6 carbon atoms.

The therapeutic value of the compounds of the invention resides in their noteworthy properties as haemostatic agents and protective agents against capillary fragility. Particular importance is due to the fact that all these compounds show much greater lipophilic character than all the other products which do not possess the alkyl group represented by R' in the general formula. It is noteworthy that the compounds according to the invention have an effect which lasts markedly longer than does that of all the other products tested before.

The sulphonation of alkylhydroquinones presents great difficulties, both when the method used is direct sulphonation by means of sulphuric acid, fuming sulphuric acid, chlorosulphonic acid or any one of their derivatives, and when gentler methods of sulphonation are used, such as the treatment of alkylquinones with alkali sulphites or bisulphites. In the first case, not only are derivatives with different degrees of sulphonation obtained, but moreover the alkyl group is frequently removed and a high proportion of p-dihydroxybenzenesulphonic acid is obtained. In the second case, a series of derivatives of highly coloured complexes forms and cannot be separated from the desired product. In both cases, the yield is so low that it is practically impossible to apply on an industrial scale.

It has now been discovered that it is possible to sulphonate alkylhydroquinones very easily and with excellent yields if bisulphites of organic bases are used for the sulphonation and the reduction of the corresponding alkylbenzoquinones and if this operation is carried out in an aprotic medium. The aprotic solvents can, for example, by cyclohexane, dioxane, chloroalkanes and the like.

Apart from the excellent yield, the process according to the invention has the advantage of avoiding carbonisation, dealkylation, the formation of polysulphonated compounds and the appearance of coloured complexes. Furthermore, the only substance which accompanies the sulphonated derivative is the alkylhydroquinone which remains dissolved in the liquid wherein the operation is carried out and which can be recovered in the pure form.

It is extremely valuable to be able to obtain, from the organic salts mentioned, the corresponding metal cation salts, either by double decomposition of the organic salt or by neutralisation of the acid, isolated beforehand by the action of a cation exchanger. Since a very pure product is used as the starting material, the salts obtained are also of great purity.

The invention is based on the fact that organic bases are generally very soluble in aprotic liquids whilst bisulphites are not. On the other hand, these bisulphites remain in a form which can be emulsified easily in the solvents, so that the following operation, that is to say the sulphonation-reduction, takes place very easily, under cold conditions or, even better, at a low temperature, and this causes the alkyl-p-dihydroxybenzenesulphonates to precipitate in a very pure form.

EXAMPLE 1

Diethylamine (tertiary butyl)-p-dihydroxybenzenesulphonate a. Production of diethylamine bisulphite 73 g of pure diethylamine (anhydrous or in which the water content has been determined beforehand) and 200 ml of pure dry dioxane are introduced into a 3-necked flask equipped with means of stirring and external cooling. The exact amount of water for the reaction (18 ml if the products are anhydrous, or the amount which makes the water content of the products present up to 18 g) is introduced into a dropping funnel. $SO_2$ gas is bubbled in slowly, with stirring. From the start, the bisulphite of the base forms as a white or yellowish mass which floats on a colourless liquid at the end of the operation. The reaction is carried out by controlling the pH which, at the end, must be $5.0 \pm 0.5$. The bisulphite obtained can be stored in the solvent at a low temperature.

b. Production of the solution of (tertiary butyl)benzoquinone (Tertiary butyl)hydroquinone is oxidised by means of a solution of sodium chlorate and vanadium oxide in dilute sulphuric acid. The precipitate of (tertiary butyl)benzoquinone dissolves in dichloromethane and the solution is isolated by decanting.

c. Production of diethylamine (tertiary butyl)-p-dihydroxybenzenesulphonate

The diethylamine bisulphite emulsion as produced under (a) is introduced into a container equipped with effective means of stirring and an ice bath. Once the temperature reaches 0° C, the solution (b) is added, with vigorous stirring. A white paste forms immediately and sticks to the bottom and to the walls of the container and to the stirrer. The operation must be carried out slowly and the additions must be spaced sufficiently far apart to prevent the formation of quinhydrones. From the moment when the liquid added no longer becomes decolorised, which indicates that the quinone is no longer reacting, the operation is stopped and the liquid part is decanted. The paste formed, which is diethylamine (tertiary butyl)-p-dihydroxybenzenesulphonate, is washed several times with dichloromethane or ether, until the wash-liquids are colourless. The resulting paste is recrystallised from ethanol or from equal parts of ethanol and water. 82 g of diethylamine (tertiary butyl)-p-dihydroxybenzenesulphonate, of melting point 185° C, are thus obtained.

EXAMPLE 2

Calcium (tertiary butyl)-p-dihydroxybenzenesulphonate

A solution of 32 g of diethylamine (tertiary butyl)-p-dihydroxybenzenesulphonate in 100 ml of distilled water is passed through a column containing 25 g of "Amberlite" IRC-50 cationic resin, and the column is washed until the eluate no longer gives the phenol reaction with a ferric chloride solution. The solution of (tertiary butyl)-p-dihydroxybenzenesulphonic acid is concentrated and a cerimetric determination is carried out on it. 23 g of this acid are obtained and are neutralised with the necessary amount of pure calcium carbonate. After several recrystallisations, 18 g of calcium (tertiary butyl)-p-dihydroxybenzenesulphonate, which melts above 240° C with decomposition, are obtained. The infra-red spectrum recorded using KBr pellets gives maxima at the following frequencies: 3,400, 2,960, 1,610, 1,500, 1,410, 1,210, 1,180, 1,050, 880, 800 and 720 $cm^{-1}$.

EXAMPLE 3

Ammonium (tertiary butyl)-p-dihydroxybenzenesulphonate

A solution of 32 g of diethylamine (tertiary butyl)-p-dihydroxybenzenesulphonate in 100 ml of distilled water, produced according to Example 1, is passed through a column containing 25 g of Amberlite IRC-50 cationic resin, and the column is washed until the eluent no longer gives the phenol reaction with a ferric chloride solution. The solution of (tertiary butyl)-p-dihydroxybenzenesulphonic acid is concentrated and a cerimetric determination is carried out on it. 23 g of this acid are thus obtained and are neutralised with the necessary amount of ammonia. After several recrystallisations, 14 g of ammonium (tertiary butyl)-p-dihydroxybenzenesulphonate, of melting point 200° C, are obtained. The infra-red spectrum recorded using KBr pellets gives maxima at the following frequencies: 1,500, 1,440, 1,170, 1,075, 1,015, 860, 820, 790 and 710 $cm^{-1}$.

The following derivatives can be produced by processes similar to those described:

1. Sodium methyl-p-dihydroxybenzenesulphonate, melting point above 240° C with decomposition.
2. Diethylamine methyl-p-dihydroxybenzenesulphonate, melting point 118° C.
3. Cyclohexylamine (tertiary butyl)-p-dihydroxybenzenesulphonate, melting point 195° C.
4. Ammonium (tertiary butyl)-p-dihydroxybenzenesulphonate, melting point 200° C.
5. Lithium (tertiary butyl)-p-dihydroxybenzenesulphonate, melting point above 265° C with decomposition. The infra-red spectrum recorded using KBr pellets gives maxima at the following frequencies: 3,400, 2,960, 1,610, 1,500, 1,440, 1,410, 1,180, 1,060, 875, 800 and 720 $cm^{-1}$.

The pharmacodynamic properties of the compounds according to the invention are illustrated below by those of diethylamine (tertiary butyl)-p-dihydroxybenzenesulphonate, prepared in Example 1 above.

1. Acute toxicity in mice

Albino mice of 18 to 25 g. The $LD_{50}$ was determined in accordance with the method of Reed and Muench.

Table I

| Method of administration | Species | $LD_{50}$ (mg/kg) | Fiducial limits |
|---|---|---|---|
| | | | (for p = 0.95) |
| intravenous | mice ♂ | 475.3 | (545 – 413.8) |
| intravenous | mice ♀ | 475 | (545 – 413.8) |
| oral | mice ♂ | 3,732 | (4,689 – 2,963) |
| oral | mice ♀ | 2,552 | (3,062 – 2,105) |

2. Effect on the average bleeding time

Diethylamine (tertiary butyl)-p-dihydroxybenzenesulphonate produces a decrease in the A.B.T. in rabbits, determined by the ROSKAM technique modified by LAPORTE (Chemotherapia, 3, 62, 1961). The results obtained one hour after the administration of the product are given in Table II.

TABLE II

| Doses micromols/kg | Effect Decrease in the A.B.T. in % |
|---|---|
| 0.625 | 7% |
| 1.25 | 25% |
| 2.5 | 34% |
| 5.0 | 42% |
| 7.05 (sic) | 49% |
| 10.0 | 55% |

3. Activity-time relationship

The effect of diethylamine (tertiary butyl)-p-dihydroxybenzenesulphonate, at a dose of 5 micromols/kg, lasts for a long time, as can be assessed from the results given in Table III.

TABLE III

| Time | Effect |
|---|---|
| hours after intravenous administration | % decrease in the A.B.T. |
| 1 | 42 |
| 2 | 43.5 |
| 4 | 41.0 |
| 8 | 34.8 |
| 16 | 33.0 |
| 24 | 22.5 |
| 48 | 14.0 |

The results given show that diethylamine (tertiary butyl)-p-dihydroxybenzenesulphonate has an effect which lasts for a markedly longer time than the products already described hitherto.

4. Protective effect on the capillaries

The effect of diethylamine (tertiary butyl)-p-dihydroxybenzenesulphonate was determined on the capillary permeability in mice, by the BEACH-STEINITZ method, in a modified form (J. Pharmacol. Exp. Ther., 131, (1), 400, 1961). When the product is administered intraperitoneally, it produces a marked decrease in the capillary permeability.

The preferred dose for humans is 1 to 2 g per day in the form of tablets, gelatine-coated pills or suppositories, and 250 to 1,000 mg per day in the form of injectable ampoules.

Example of a formulation for a tablet
Diethylamine (tertiary butyl)-p-dihydroxybenzenesulphonate    0.500 g

| -continued | |
|---|---|
| Rice starch | 0.100 g |
| Lactose | 0.100 g |
| Polyvinylpyrrolidone | 0.020 g |
| Magnesium stearate | 0.003 g |
| Weight of tablet | 0.723 g |
| *Example of a formulation for a gelatine-coated pill* | |
| Diethylamine (tertiary butyl)-p-dihydroxybenzenesulphonate | 0.250 g |
| Lactose | 0.050 g |
| Aerosil | 0.001 g |
| Magnesium stearate | 0.002 g |
| Weight of gelatine-coated pill | 0.303 g |
| *Example of a formulation for a suppository* | |
| Diethylamine (tertiary butyl)-p-dihydroxybenzenesulphonate | 0.500 g |
| Citric acid | 0.0036 g |
| Sodium metabisulphite | 0.0002 g |
| Monolene | 1.650 g |
| Weight of suppository | 2.15 g |
| *Example of a formulation for an injectable ampoule* | |
| Diethylamine (tertiary butyl)-p-dihydroxybenzenesulphonate | 0.250 g |
| Sodium metabisulphite | 0.002 g |
| Distilled water | 4 ml |

The pharmacological data of some examples of the invention as well as the partition coefficients of the products are summarised in a table below.

The acute toxicity in mice was determined in accordance with the method of REED and MUENCH, in a modified form (Reed L. J. and Muench H., Am. J. Hyg., 27, 493, 1938). The effect on the average bleeding time was determined by the Roskam technique modified by Laporte (Laporte J., Chemotherapia, 3, 62, 1961).

In relation to the daily dose for humans, administered in various pharmaceutical forms, a guide-line dose is indicated in the table.

|  | $LD_{50}$* (mg/kg) | $ED_{50}$** | Partition coefficient butanol/water | Proposed dose | | |
|---|---|---|---|---|---|---|
|  |  |  |  | rectal | oral | parenteral |
| Diethylamine (tertiary butyl)-p-dihydroxybenzenesulphonate (Ex. 1) | 475 (i.v.) | 1.60 | 2.38 | 1–2 | 1–2 | 0.25–1 |
| Calcium (tertiary butyl)-p-dihydroxybenzenesulphonate (Ex. 2) | 2,337 (p.o.) | 1.75 | 1.36 | 1–2 | 1–2 | 0.25–1 |
| Sodium methyl-p-dihydroxybenzenesulphonate | >1,000 (p.o.) | 1.95 | 0.87 | 1–2 | 1–2 | 0.25–1 |
| Cyclohexylamine (tertiary butyl)-p-dihydroxybenzenesulphonate | 1,000 (p.o) | 0.90 | 10.05 | 1–2 | 1–2 | 0.25–1 |
| Lithium (tertiary butyl)-p-dihydroxybenzenesulphonate | 1,000 (i.v.) | 0.95 | 1.28 | 1–2 | 1–2 | 0.25–1 |
| Ammonium (tertiary butyl)-p-dihydroxybenzenesulphonate | 600 (i.v.) | 1.0 | 0.42 | 1–2 | 1–2 | 0.25–1 |

*LD: lethal dose
**ED: effective dose

I claim:

1. A medicament having a hemostatic effect and a protective effect on the capillaries, comprising a pharmaceutically acceptable carrier and a hemostatically effective amount of a compound of the formula.

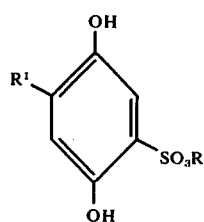

in which $R^1$ is selected from the group consisting of a linear and a branched alkyl group with 1 to 6 carbon atoms and R is selected from the group consisting of lithium, sodium, ammonium an equivalent of calcium, the cation of a lower alkyl amine and the cation of cyclohexylamine.

2. A medicament having a hemostatic effect and a protective effect on the capillaries, comprising a pharmaceutically acceptable carrier and a hemostatically effective amount of diethylamine (tertiary butyl)-p-dihydroxybenzenesulphonate (Ex. 1).

3. A medicament having a hemostatic effect and a protective effect on the capillaries, comprising a pharmaceutically acceptable carrier and a hemostatically effective amount of calcium (tertiary butyl)-p-dihydroxybenzenesulphonate (Ex. 2).

4. A medicament having a hemostatic effect and a protective effect on the capillaries, comprising a pharmaceutically acceptable carrier and a hemostatically effective amount of sodium methyl-p-dihydroxybenzenesulphonate.

5. A medicament having a hemostatic effect and a protective effect on the capillaries, comprising a pharmaceutically acceptable carrier and a hemostatically effective amount of cyclohexylamine (tertiary butyl)-p-dihydroxybenzenesulphonate.

6. A medicament having a hemostatic effect and a protective effect on the capillaries, comprising a pharmaceutically acceptable carrier and a hemostatically effective amount of lithium (tertiary butyl)-p-dihydroxybenzenesulphonate.

7. A medicament having a hemostatic effect and a protective effect on the capillaries, comprising a pharmaceutically acceptable carrier and a hemostatically effective amount of ammonium (tertiary butyl)-p-dihydroxybenzenesulphonate.

8. The process which comprises administering orally or rectally at the dose for humans of 1 to 2 g per day, or administered parenterally at the dose for humans of 250 to 1,000 mg per day of the composition set forth in claim 1.

9. The process which comprises administering orally or rectally at the dose for humans of 1 to 2 g per day, or administered parenterally at the dose for humans of 250 to 1,000 mg per day of the composition set forth in claim 2.

10. The process which comprises administering orally or rectally at the dose for humans of 1 to 2 g per day, or administered parenterally at the dose for humans of 250 to 1,000 mg per day of the composition set forth in claim 3.

11. The process which comprises administering orally or rectally at the dose for humans of 1 to 2 g per day, or administered parenterally at the dose for humans of 250 to 1,000 mg per day of the composition set forth in claim 4.

12. The process which comprises administering orally or rectally at the dose for humans of 1 to 2 g per day, or administered parenterally at the dose for humans of 250 to 1,000 mg per day of the composition set forth in claim 5.

13. The process which comprises administering orally or rectally at the dose for humans of 1 to 2 g per day, or administered parenterally at the dose for humans of 250 to 1,000 mg per day of the composition set forth in claim 6.

14. The process which comprises administering orally or rectally at the dose for humans of 1 to 2 g per day, or administered parenterally at the dose for humans of 250 to 1,000 mg per day of the composition set forth in claim 7.

* * * * *